United States Patent
Hoess et al.

(10) Patent No.: US 8,927,230 B2
(45) Date of Patent: Jan. 6, 2015

(54) C-TERMINAL MODIFICATION OF POLYPEPTIDES

(71) Applicant: Frank Bordusa, Rossbach (DE)

(72) Inventors: Eva Hoess, Neuried (DE); Frank Bordusa, Rossbach (DE); Rupert Hermann, Weilheim (DE); Hans-Dieter Jakubke, Dresden-Langebrueck (DE); Wilhelm Tischer, Peissenberg (DE)

(73) Assignee: EUCODIS Bioscience GmbH, Vienna (AT)

( * ) Notice: Subject to any disclaimer, the term of this patent is extended or adjusted under 35 U.S.C. 154(b) by 0 days.

(21) Appl. No.: 13/741,206

(22) Filed: Jan. 14, 2013

(65) Prior Publication Data

US 2013/0177940 A1    Jul. 11, 2013

Related U.S. Application Data

(63) Continuation of application No. 11/704,561, filed on Feb. 9, 2007, now abandoned, which is a continuation of application No. PCT/EP2005/008809, filed on Aug. 12, 2005.

(30) Foreign Application Priority Data

Aug. 13, 2004    (EP) .................................... 04019237

(51) Int. Cl.
*C12P 21/06*    (2006.01)
*C12N 9/64*    (2006.01)
*C12N 9/76*    (2006.01)

(52) U.S. Cl.
CPC ............... *C12N 9/6424* (2013.01); *C12P 21/06* (2013.01); *C12N 9/6427* (2013.01)
USPC ...................................................... 435/68.1

(58) Field of Classification Search
CPC combination set(s) only.
See application file for complete search history.

(56) References Cited

U.S. PATENT DOCUMENTS

| | | | |
|---|---|---|---|
| 5,580,751 A | 12/1996 | Buchardt et al. | |
| 5,985,627 A | 11/1999 | Mortensen et al. | |
| 2004/0034197 A1 | 2/2004 | Bordusa et al. | |

FOREIGN PATENT DOCUMENTS

| | | |
|---|---|---|
| WO | WO9118294 | 11/1991 |
| WO | WO9418329 | 8/1994 |
| WO | WO 9520039 | 7/1995 |
| WO | WO 9603409 | 2/1996 |

OTHER PUBLICATIONS

Willett et al., Engineered metal regulation of trypsin specificity, Biochemistry (1995) 34(7):2172-2180.
Rail et al., Engineering of trypsin for substrate mimetics-mediated peptide synthesis, Peptides 2000, Proceedings of the European Peptide Symposium, 26th, Montpellier, France, Sep. 10-15, 2000, (2001) pp. 339-340.
Galye et al., Identification of regions in interleukin-1 alpha important for activity, J Bioi Chem., 1993, 268(29):22105-22111.
Whisstock et al., Prediction of protein function from protein sequence and structure, Q Rev Biophys., 2003, 36(3):307-340.
Kurth et al., Engineering the S1' subsite of trypsin: design of a protease which cleaves between dibasic residues, Biochemistry, 1998,37(33): 11434-11440.
Brinen et al., X-ray structures of a designed binding site in trypsin show metal-dependent geometry, Biochemistry, 1996, 35(19):5999-6009.
pdb1 slx_bvsSID1 from Brinen et al., X-ray structures of a designed binding site in trypsin show metal-dependent geometry, Biochemistry, 1996, 35(19):5999-6009. Alignment with SEQ ID No. 1.
pdb1 slx_b from Brinen et al., X-ray structures of a designed binding site in trypsin show metal-dependent geometry, Biochemistry, 1996, 35(19):5999-6009.
Bongers J et al., International journal of peptide and Protein Research 1992, vol. 40, No. 3-4, pp. 268-273.
Goepfert A et al., "Peptide synthesis during in vitro proteolysis—transpeptidation or condensation?" Die Nahrung, 1999, vol. 43, No. 3, pp. 211-212.
Hartley B S and Shotton D M, The Enzymes (PD. Boyer, ed), vol. 3, 1971, pp. 323-373.
Jonczyk A et al., Hoppe-Seyler's Zeitschrift für Physiologische Chemie, Dec. 1981, vol. 362, No. 12, pp. 1591-1598.
Schechter J, Berger A, Biochem Biophys Res Commun 27, 1967, pp. 157-162.
Stennicke H. R. et al., Anal. Biochem. 248, 1997, pp. 141-148.
Allen J B et al., TIBS 20, 1995, pp. 511-516.
Barlos et al., Tetrahedron Lett 30, 1989, 3947.
Blaschke, U.K. et al., Methods Enzymol. 328, 2000, pp. 478-496.
Hedstrom L, et al., Science 255, 1992, pp. 1249-1253.
Hochuli E et al., J Chromatogr 411, 1987, pp. 177-184.
Mao H. et al., J Am Chem Soc 126, 2004, pp. 2670-2671.
Wang S S, J Am Chem Soc 95, 1973, pp. 1328-1333.

*Primary Examiner* — Sheridan Swope
(74) *Attorney, Agent, or Firm* — Michael Fedrick; Loza & Loza, LLP

(57) ABSTRACT

The invention relates to a mutated trypsin comprising an amino acid substitution both at position K60 and D189, and at least one more amino acid substitution by histidine at position N143 or position E151. Such trypsin mutant has a preferred cleavage site comprising the amino acids $Xaa_1$-$Xaa_2$-His, wherein $Xaa_1$ is L, Y or F and $Xaa_2$ is R or K. The invention also relates to a man-made polypeptide comprising a target peptide and the above cleavage site as well as to a method of producing C-terminally modified target peptides by using this mutated trypsin.

4 Claims, 5 Drawing Sheets a)

b)

SEQUENCE LISTING

```
<160> NUMBER OF SEQ ID NOS: 24

<210> SEQ ID NO 1
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 1

Ile Val Gly Gly Tyr Thr Cys Gln Glu Asn Ser Val Pro Tyr Gln Val
1               5                   10                  15

Ser Leu Asn Ser Gly Tyr His Phe Cys Gly Gly Ser Leu Ile Asn Asp
            20                  25                  30

Gln Trp Val Val Ser Ala Ala His Cys Tyr Glu Ser Arg Ile Gln Val
        35                  40                  45

Arg Leu Gly Glu His Asn Ile Asn Val Leu Glu Gly Asn Glu Gln Phe
    50                  55                  60

Val Asn Ala Ala Lys Ile Ile Lys His Pro Asn Phe Asp Arg Lys Thr
65                  70                  75                  80

Leu Asn Asn Asp Ile Met Leu Ile Lys Leu Ser Ser Pro Val Lys Leu
                85                  90                  95

Asn Ala Arg Val Ala Thr Val Ala Leu Pro Ser Ser Cys Ala Pro Ala
            100                 105                 110

Gly Thr Gln Cys Leu Ile Ser Gly Trp Gly His Thr Leu Ser Ser Gly
        115                 120                 125

Val Asn His Pro Asp Leu Leu Gln Cys Leu Asp Ala Pro Leu Leu Pro
    130                 135                 140

Gln Ala Asp Cys Glu Ala Ser Tyr Pro Gly Lys Ile Thr Asp Asn Met
145                 150                 155                 160

Val Cys Val Gly Phe Leu Glu Gly Gly Lys Lys Ser Cys Gln Gly Asp
                165                 170                 175

Ser Gly Gly Pro Val Val Cys Asn Gly Glu Leu Gln Gly Ile Val Ser
            180                 185                 190

Trp Gly Tyr Gly Cys Ala Leu Pro Asp Asn Pro Gly Val Tyr Thr Lys
        195                 200                 205

Val Cys Asn Tyr Val Asp Trp Ile Gln Asp Thr Ile Ala Ala Asn
    210                 215                 220
```

```
<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Ala Ala Tyr Arg His Ala Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Ala Ala Tyr Arg His Ala Ala Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Ala Ala Tyr Arg His Asp Ala Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Ala Ala Tyr Arg Arg Ala Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ala Ala Tyr Asp His Ala Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ala Ala Tyr Lys His Ala Gly
1               5

<210> SEQ ID NO 8
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Ala Ala Tyr Arg His Tyr Ala Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ala Ala Phe Arg His Ala Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Ala Ala Tyr Arg His Arg Ala Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Ala Ala Leu Arg His Ala Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ala Ala Phe Lys His Ala Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Ala Ala Tyr Ala His Ala Gly
1               5

<210> SEQ ID NO 14
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 14

Ala Ala Tyr Arg Ala Ala Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ala Ala Arg Arg His Ala Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

Ala Ala Ala Arg His Ala Gly
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ala Ala Tyr Arg Asn Ala Gly
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Ala Ala Asp Arg His Ala Gly
1               5

<210> SEQ ID NO 19
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 19

Ala Lys Thr Ala Ala Ala Leu His Ile Leu Val Lys Glu Glu Lys Leu
1               5                   10                  15

Ala Leu Asp Leu Leu Glu Gln Ile Lys Asn Gly Ala Asp Phe Gly Lys
            20                  25                  30

Leu Ala Lys Lys His Ser Ile Cys Pro Ser Gly Lys Arg Gly Gly Asp
```

```
                    35                  40                  45
Leu Gly Glu Phe Arg Gln Gly Gln Met Val Pro Ala Phe Asp Lys Val
        50                  55                  60

Val Phe Ser Cys Pro Val Leu Glu Pro Thr Gly Pro Leu His Thr Gln
65                  70                  75                  80

Phe Gly Tyr His Ile Ile Lys Val Leu Tyr Arg His
                85                  90

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD RES
<222> LOCATION: (3)..(3)
<223> OTHER INFORMATION: Asp, Glu, Ala, Asn, Gln or Lys

<400> SEQUENCE: 20

Leu Pro Xaa Thr Gly
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic peptide

<400> SEQUENCE: 21

Ala Ala Tyr Arg
1

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Ala Ala Tyr Arg His Lys
1               5

<210> SEQ ID NO 23
<211> LENGTH: 4
<212> TYPE: PRT
<213> ORGANISM: Artificial Sequence
<220> FEATURE:
<223> OTHER INFORMATION: Synthetic peptide

<400> SEQUENCE: 23

Arg His Ala Lys
1

<210> SEQ ID NO 24
<211> LENGTH: 93
<212> TYPE: PRT
<213> ORGANISM: Artificial Sequence
<220> FEATURE:
<223> OTHER INFORMATION: Synthetic polypeptide

<400> SEQUENCE: 24

Ala Lys Thr Ala Ala Ala Leu His Ile Leu Val Lys Glu Glu Lys Leu
1               5                   10                  15
```

-continued

```
Ala Leu Asp Leu Leu Glu Gln Ile Lys Asn Gly Ala Asp Phe Gly Lys
            20                  25                  30

Leu Ala Lys His Ser Ile Cys Pro Ser Gly Lys Arg Gly Gly Asp
        35              40                  45

Leu Gly Glu Phe Arg Gln Gly Gln Met Val Pro Ala Phe Asp Lys Val
    50                  55                  60

Val Phe Ser Cys Pro Val Leu Glu Pro Thr Gly Pro Leu His Thr Gln
65                  70                  75                  80

Phe Gly Tyr His Ile Ile Lys Val Leu Tyr Arg His Gly
                85                  90
```

C-TERMINAL MODIFICATION OF POLYPEPTIDES

CROSS-REFERENCE TO RELATED APPLICATIONS

This application is a continuation of U.S. patent application Ser. No. 11/704,561, filed Feb. 9, 2007, which is abandoned, which is a continuation of International Patent Application No. PCT/EP2005/008809, filed Aug. 12, 2005, which is abandoned, and which claims priority under 35 U.S.C. §119 to European Patent Application No. 04019237.9, filed Aug. 13, 2004. The disclosures of the foregoing patent applications are incorporated herein by reference in their entirety.

SEQUENCE LISTING

The entire content of a Sequence Listing titled "Sequence_Listing.txt," created on May 27, 2014 and having a size of 8 kilobytes, which has been submitted in electronic form in connection with the present application, is hereby incorporated by reference herein in its entirety.

BACKGROUND

The present invention relates to a mutated trypsin comprising an amino acid substitution both at position K60 and D189, and at least one more amino acid substitution by histidine at position N143 or position E151. Such trypsin mutant has a preferred cleavage site comprising the amino acids $Xaa_1$-$Xaa_2$-His, wherein $Xaa_1$ is L, Y or F and $Xaa_2$ is R or K. The invention also relates to a man-made polypeptide comprising a target peptide and the above cleavage site as well as to a method of producing C-terminally modified target peptides by using this mutated trypsin.

The use of biologically active peptides, e.g. for pharmaceutical purposes has become more and more important during the past years. Several methods exist to produce such biologically active peptides, for example, the chemical synthesis based on solid phase or solution phase peptide synthesis techniques, or the cultivation of genetically manipulated microorganisms followed by the isolation and purification of such produced recombinant proteins.

However, it remains difficult and costly to chemically synthesize polypeptides of more than about 50 amino acids. It also represents a significant task to modify a peptide obtained by chemical peptide synthesis and/or a recombinantly obtained polypeptide at its C-terminal end. One of the most powerful methods to modify polypeptides is through a controlled protein ligation, whereby peptide analogs, unnatural amino acids, stable isotopes, fluorophores, and other biochemically or biophysically important molecules can be specifically incorporated into a polypeptide. One of these methods is based on the introduction—mostly synthetically—of a chemo-selective amino acid, mainly a cysteine which then is modified by a thio-selective reagent attacking the SH-side chain of this amino acid residue. A further alternative is the so-called intein-based protein ligation system, which can generate a protein thioester by proteolysis of a corresponding protein-intein fusion protein (Blaschke, U.K., et al., Methods Enzymol. 328 (2000) 478-496). This method has been successfully applied to introduce unnatural modifications into proteins. However, difficulties remain, e.g., because the target protein must be expressed as a fusion protein together with an intein.

Recently a few more enzyme-based approaches for peptide ligation and/or C-terminal modification have been described. Breddam and co-workers (e.g., U.S. Pat. No. 5,985,627) describe the use of the serine protease carboxypeptidase Y (CPD-Y) in the C-terminal modification of peptides with fluorescence or affinity labels. This modification is based on the specific ability of CPD-Y to stepwise cleave amino acids off the C-terminal end of polypeptides. This method therefore may be considered to be a specific tool for modification of the C-terminus of a polypeptide. CPD-Y cleaves off the C-terminal amino acid under formation of a peptide-acyl-enzyme-intermediate. This acyl-enzyme-intermediate upon nucleophilic attack is deacylated resulting in a transamidation reaction. The desired transamidation reaction may be accompanied by (un-wanted) side reactions like hydrolysis. It is also possible that more than one C-terminal amino acid is cleaved off, on the other hand also amino acids may be added by this method (Stennicke, H. R., et al., Anal. Biochem. 248 (1997) 141-148 and Buchardt, O., et al., U.S. Pat. No. 5,580,751)

Abrahmson et al. (e.g. WO 94/18329) described the use of serine protease variants for ligation of peptides. Subtilisin variants are disclosed which have an improved peptide ligase activity. It is, however, necessary for effective peptide ligation to use an appropriate amino terminus protecting group and an appropriate carboxy terminus activating group, respectively, in order to efficiently ligate two peptide substrates.

Recently sortase-mediated protein ligation has been described as an alternative method in protein engineering (Mao, H., et al., J. Am. Chem. Soc. 126 (2004) 2670-2671). Sortase, an enzyme isolated from *Staphylococcus aureus* catalyses a transpeptidation reaction by cleaving between threonine and glycine in a recognition motif consisting of the amino acids LPXTG (SEQ ID NO: 20) and subsequently joining the carboxyl group of threonine to an N-terminal glycine. In nature it catalyses the transpeptidation of the threonine to an amino group of pentaglycine on the cell wall peptidoglycan.

In the sortase recognition motif LPXTG (SEQ ID NO: 20), X may be the amino acids D, E, A, N, Q, or K. This enzyme has been used to ligate carboxy terminal threonine residues of a peptide or a protein to an N-terminal glycine of a second peptide. As mentioned, sortase requires a recognition motif of five amino acids of which four amino acids (LPXT) will be present within the ligation product.

Therefore, whereas several methods exist for C-terminal modification of polypeptides there is a tremendous need for alternative or improved methods of C-terminal modification of polypeptides. The inventors of the present invention have found that it is possible to use special trypsin mutants in the C-terminal modification of polypeptides.

SUMMARY OF THE INVENTION

In one embodiment that present invention therefore relates to a mutated trypsin comprising an amino acid substitution both at position K60 and D189, and at least one amino acid substitution by histidine at position N143 or position E151 according to the chymotrypsin nomenclature which corresponds to positions 43, 171, 123, and 131, respectively, of the sequence given in SEQ ID NO: 1.

The skilled artisan is familiar with the so-called chymotrypsin nomenclature as, e.g., described in Hartley, B. S., and Shotton, D. M., The Enzymes, P. D. Boyer (ed.), Vol. 3, (1971), pp. 323-373 and will have no problem in aligning the positions of a variant trypsin with positions given according to the chymotrypsin nomenclature to the corresponding ones of the trypsin sequence of SEQ ID No: 1.

Position 60 according to chymotrypsin nomenclature corresponds to position 43 of the sequence of mature anionic rat trypsin II from Rattus norvegicus as given in SEQ ID NO: 1.

Position 143 according to chymotrypsin nomenclature corresponds to position 123 of the sequence of mature anionic rat trypsin II from Rattus norvegicus as given in SEQ ID NO: 1.

Position 151 according to chymotrypsin nomenclature corresponds to position 131 of the sequence of mature anionic rat trypsin II from Rattus norvegicus as given in SEQ ID NO: 1.

Position 189 according to chymotrypsin nomenclature corresponds to position 171 of the sequence of mature anionic rat trypsin II from Rattus norvegicus as given in SEQ ID NO: 1.

Since the skilled artisan is used to express positions referring to the chymotrypsin nomenclature, therefore, in the following the references to specific sequence position, e.g., position K60 or simply position 60 are exclusively based on positions according to the chymotrypsin nomenclature.

The present invention also relates to the use of a man-made polypeptide comprising a target peptide and a restriction site peptide comprising the cleavage site $Xaa_1$-$Xaa_2$-His, wherein $Xaa_1$ is L, Y or F, and $Xaa_2$ is R or K, wherein said restriction site peptide overlaps with the target peptide by the amino acid $Xaa_1$ at the C-terminal end of said target peptide as a substrate of a trypsin mutant as disclosed in the present invention.

Also provided is a method of producing a C-terminally transacylated target peptide comprising the steps of: (a) providing a polypeptide comprising a target peptide and a restriction site peptide comprising the cleavage site $Xaa_1$-$Xaa_2$-His, wherein $Xaa_1$ is L, Y or F, and $Xaa_2$ is R or K, wherein said restriction site peptide overlaps with the target peptide by the amino acid $Xaa_1$ at the C-terminal end of said target peptide, (b) bringing said peptide into contact with a trypsin mutant according to the present invention under conditions allowing for endoproteolytic cleavage after $Xaa_1$ and formation of an endoprotease target peptide-acyl-intermediate, (c) adding an appropriate nucleophile, and (d) upon nucleophilic attack and binding said nucleophile to the C-terminus of the target peptide releasing the mutated trypsin from the endoprotease target peptide-acyl-intermediate.

In a further embodiment the present invention relates to nucleotide sequences coding for the novel trypsin mutants, to vectors comprising such mutants and to transformed host cells comprising such vectors.

The mutated trypsin according to the present invention is a trypsin comprising amino acid substitutions at both the positions K60 and D189 and at least one amino acid substitution at position N143 or at position E151. The substitution in position 143 and/or position 151 is by histidine (His).

Preferably the mutated trypsin according to the present invention comprises either the amino acid E or the amino acid D in position 60, thus replacing the amino acid K normally present in position 60.

It is also preferred that the mutated trypsin according to the present invention comprises either the amino acid K, the amino acid H, or the amino acid R in position 189, thus replacing amino acid D normally present in that position. A very preferred substitution is with K at position 189.

In a further preferred embodiment the mutated trypsin according to the present invention comprises mutations in positions 60, 143, 151 and 189. Preferred substitutions in this mutated enzyme are K60E or D, N143H, E151H and D189K or R.

The above described mutants of trypsin have very interesting and important properties. Such mutants appear to preferentially recognize a binding or cleavage site consisting of 3 amino acids $Xaa_1$-$Xaa_2$-His, wherein $Xaa_1$ is L, Y or F and $Xaa_2$ is R or K. This restriction site is cleaved by the above mutants after $Xaa_1$. This is a very important feature, because by using the novel trypsin mutants only one amino acid, i.e. the C-terminal $Xaa_1$, will remain within the modified target polypeptide.

On the left a schematic for the E. coli shuttle vector pST, comprising a coding region for trypsinogen is shown. The coding region can be easily inserted into a pYT-vector, optimized for polypeptide expression in yeast. A schematic of a pYT-vector comprising a coding region for trypsinogen is given on the right hand of this figure.

Figure 2:
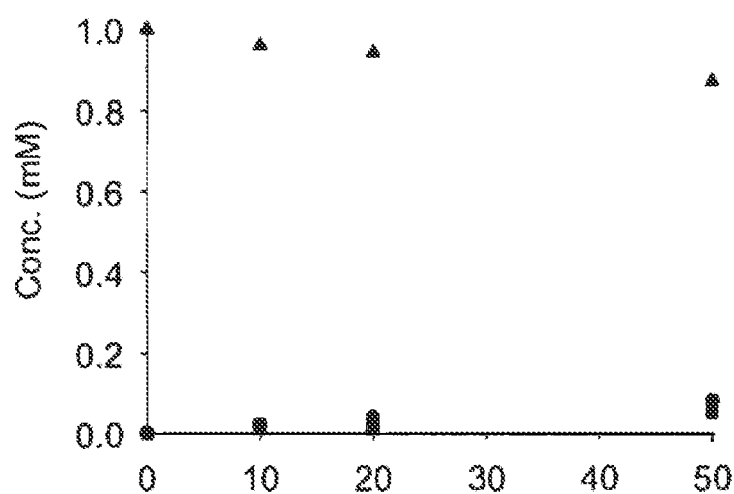
Figure 2:
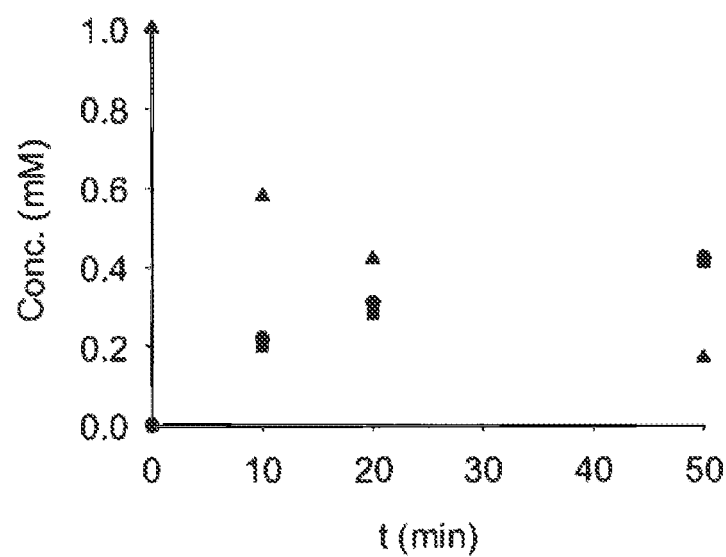

FIG. 2: Kinetics of transamidation

Time course of the transamidation of Ala-Ala-Tyr-Arg-His-Ala-Gly (SEQ ID NO: 2, triangles) with Arg-NH2 catalyzed by the trypsin variant Tn K60E, E151H, N143H, D189K resulting in Ala-Ala-Tyr-Arg-NH2 (SEQ ID NO: 21, circles) in the presence of a) 100 μM EDTA or b) 100 μM $ZnCl_2$. Squares represent AAY, which is formed as a side product of reaction due to proteolysis.

Figure 3:
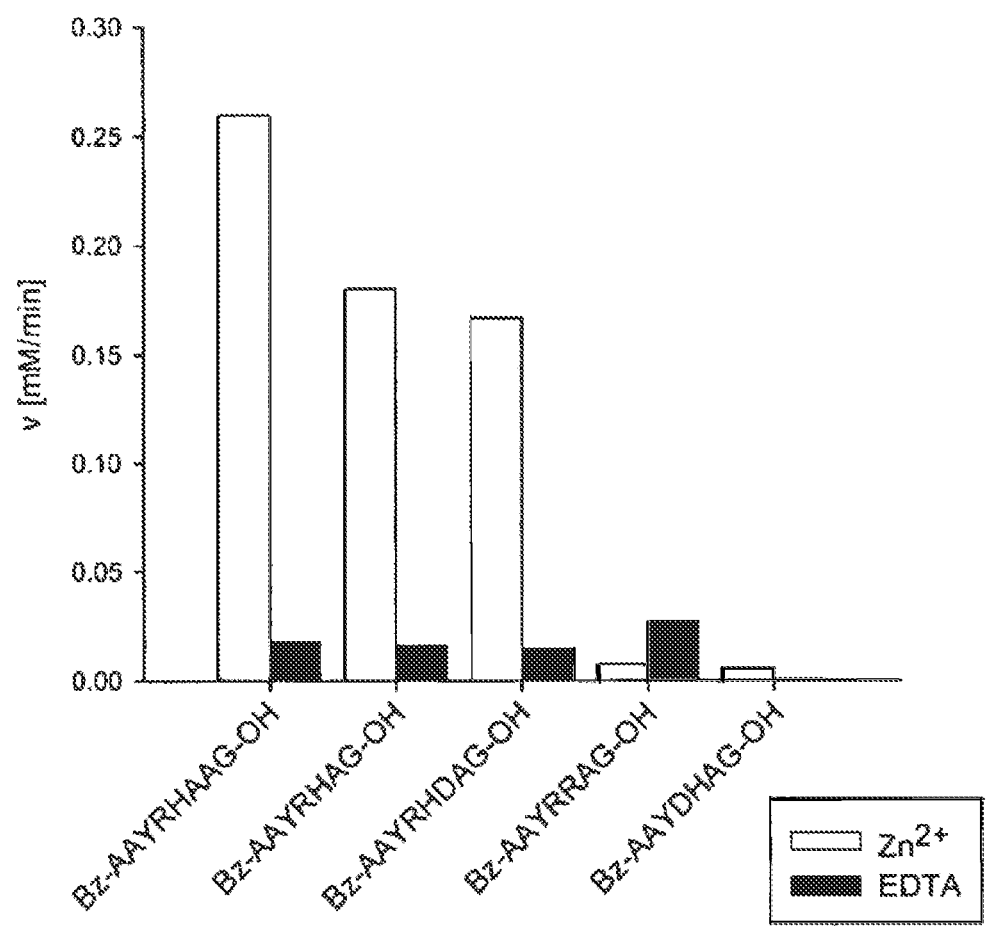

FIG. 3: Influence of $Zn^{2+}$ on catalytic activity. Figure discloses SEQ ID NOS 3, 2, 4, 5, and 6, respectively, in order of appearance.

The influence of the presence (grey bars) or absence (black bars) of $Zn^{2+}$ ions on the rate of peptide turnover by trypsin variant Tn K60E, E151H, N143H, D189K is shown.

Figure 4:
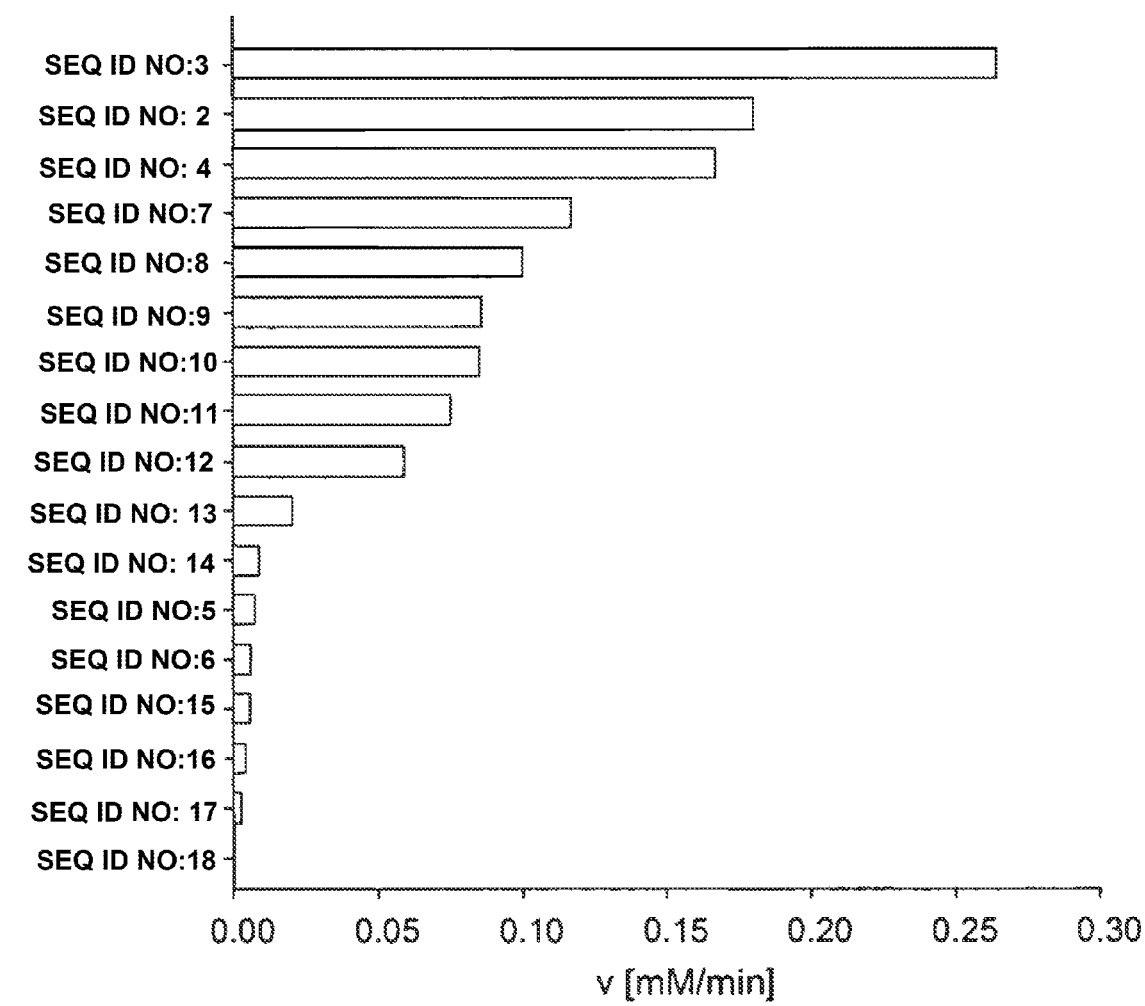

FIG. 4: Influence of the recognition sequence on the rate of reaction catalyzed by the trypsin variant Tn K60E, E151H, N143H, D189K-catalyzed Variant trypsin according to the present invention has been tested for catalytic activity upon peptide substrates with different peptide sequences at or close to the cleavage site. The initial rate (v) of peptide consumption is given in nM/min FIG. 5: Mass spectrum of Bz-Ala-Ala-Tyr-Arg-His-Lys (6-CF)—OH (SEQ ID NO: 22).

DETAILED DESCRIPTION OF THE INVENTION

To facilitate an understanding of the invention, a brief discussion of the terminology used in connection with the invention will be provided. The present disclosure uses the terminology of Schechter, J., and Berger, A., Biochem. Biophys. Res. Commun. 27 (1967) 157-162, to describe the location of various amino acid residues on the peptide substrate and within the active site of a corresponding proteolytic enzyme.

According to the terminology proposed by Schechter, J. and Berger, A., supra, the amino acid residues of the peptide substrate are designated by the letter "P". The amino acids of the substrate on the N-terminal side of the peptide bond to be cleaved (the "cleavage site") are designated $P_n \ldots P_3, P_2, P_1$ with $P_n$ being the amino acid residue furthest from the cleavage site. Amino acid residues of the peptide substrate on the C-terminal side of cleavage site are designated $P_1', P_2', P_3' \ldots P_n'$ with $P_n'$ being the amino acid residue furthest from the cleavage site. Hence, the bond which is to be cleaved (the "cleavage site") is the $P_1$—$P_1'$ bond.

The generic formula for the amino acids of the substrate of an endopeptidase (like for example trypsin) is as follows:

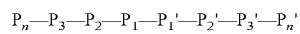

The designation of the substrate binding sites of an endopeptidase is analogous to the designation of amino acid residues of the peptide substrate. However, the binding sub sites of an endopeptidase are designated by the letter "S" and can include more than one amino acid residue. The substrate binding sites for the amino acids on the N-terminal site of the cleavage site are labeled $S_n \ldots S_3, S_2, S_1$. The substrate binding sub site for the amino acids on the carboxy side of the cleavage site are designated $S_1', S_2', S_3', S_n'$. Hence, in an endopeptidase, the $S_1'$ sub site interacts with the $P_1'$ group of the peptide substrate and the incoming nucleophile. A generic formula for describing substrate binding sites of an endopeptidase is:

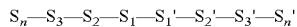

The $S_1$ binding site binds the side chain of the penultimate amino acid, $P_1$, of the peptide substrate, in case of a trypsin mutant according to this invention the amino acid $Xaa_1$. The $S_1'$ binding site interacts with the side chain of $P_1'$, in the present case with $Xaa_2$. Likewise, the $S_2'$ binding site interacts with the side chain of the histidine residue in position $P_2'$.

As the skilled artisan will appreciate the present invention may also be carried out with trypsin variants comprising an amino acid substitution both at position K60 and D 189, and at least one more amino acid substitution by histidine at position N143 or position E151.

The term "variant" refers to polypeptides having amino acid sequences that differ to some extent from a native polypeptide sequence. Ordinarily, a variant amino acid sequence will possess at least about 80% homology with the corresponding parent trypsin sequence, and preferably, it will be at least about 90%, more preferably at least about 95% homologous with such corresponding parent trypsin sequence. The amino acid sequence variants possess substitutions, deletions, and/or insertions at certain positions within the amino acid sequence of the native amino acid sequence. Preferably sequence homology will be at least 96% or 97%.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

Preferably, a variant of trypsin as disclosed in the present invention in comparison to the corresponding wild-type sequence, comprises 20 amino acid substitutions or less, more preferred 15 amino acid substitutions or less, also preferred 10 amino acid substitutions or less, and also preferred 6 amino acid substitutions or less.

The modified trypsin of the invention is capable of improved transacylation when compared to the corresponding native trypsin. As used herein, "transacylation" is a reaction in which a peptide fragment C-terminal to the trypsin cleavage site is exchanged for a nucleophile. Transacylation reactions include transthiolation, transesterification and transamidation reactions. "Transamidation" occurs when an amide bond is formed between the nucleophile and the target peptide substrate. In a transamidation reaction, the nucleophile is not necessarily an amino acid. "Transpeptidation" as an important subgroup of transamidation occurs when the nucleophile is an amino acid, or amino acid derivative, such as an amino acid ester or amino acid amide.

A general transacylation reaction according to the present invention is shown below:

$$P_n-P_3-P_2-Xaa_1-Xaa_2-His-P_3'-P_n' + N \rightarrow P_n-P_3-P_2-Xaa_1-N + Xaa_2-His-P_3'-P_n'$$

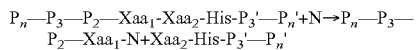

In the first step, the enzyme attacks the peptide bond between $Xaa_1$ and $Xaa_2$, displacing the more C-terminal amino acids and forming a covalent (an acyl) bond between the $P_1$ residue ($Xaa_1$) of the target peptide and the enzyme. This intermediate is referred to as a target peptide "peptide-acyl-enzyme intermediate" or briefly as acyl-enzyme intermediate. In the presence of an appropriate nucleophile, under proper conditions, the enzyme causes the nucleophile to add to the cleaved peptide substrate to produce a transacylated product. It is believed that the nucleophile attaches to the carboxyl group of the acyl-enzyme intermediate and displaces the enzyme from the acyl-enzyme intermediate. In this manner, the nucleophile becomes linked to the carboxyl group of the peptide substrate.

Instead of undergoing a transacylation reaction, the acyl-enzyme intermediate might be deacylated by water to produce a hydrolysis product. The mutated trypsin of the invention is designed to preferentially produce the transacylation product over the hydrolysis product.

The present invention also relates to a man-made polypeptide comprising a target peptide and a restriction site peptide comprising the cleavage site $Xaa_1$-$Xaa_2$-His, wherein $Xaa_1$ is L, Y or F, and $Xaa_2$ is R or K, wherein said restriction site peptide overlaps with the target peptide by the amino acid $Xaa_1$ at the C-terminal end of said target peptide. With other words it relates to a man-made polypeptide comprising a target peptide and a restriction site peptide comprising the cleavage site $Xaa_1$-$Xaa_2$-His, wherein $Xaa_1$ is L, Y or F, and $Xaa_2$ is R or K, wherein said restriction site peptide and said target peptide share the amino acid $Xaa_1$ at the C-terminal end of said target peptide. More preferred $Xaa_1$ is Y or F, and especially preferred $Xaa_1$ is Y.

The term target peptide thus refers to the peptide or polypeptide of the sequence $P_n-P_3-P_2-Xaa_1$. The target peptide thus includes one amino acid of the cleavage site for the mutated trypsin of this invention, i.e., the amino acid $Xaa_1$, being either L, Y or F. The term peptide does include polypeptides.

The term man-made is used to indicate that the peptide sequence is artificial, e.g. it has been designed by a scientist or by a computer. The present invention does not relate to naturally occurring polypeptides comprising the above-defined sequence motif $Xaa_1$-$Xaa_2$-His. It merely relates, to man-made, e.g. synthetically or recombinantly produced polypeptides which have been designed to comprise both a target polypeptide as well as a restriction site peptide to comprise the cleavage site $Xaa_1$-$Xaa_2$-His with $Xaa_1$ and $Xaa_2$ as defined above. According to our definition the target polypeptide has the amino acid $Xaa_1$ as its C-terminal amino acid. The restriction site peptide comprises at least the amino acids $Xaa_2$-His and optionally C-terminal thereto further amino acids. Thus the cleavage site consisting of $Xaa_1$-$Xaa_2$-His overlaps with the target polypeptide by one amino acid ($Xaa_1$) and by two amino acids ($Xaa_2$-His) with the restriction site peptide. As this skilled artisan will appreciate in principle any polypeptide comprising $Xaa_1$-$Xaa_2$-His wherein $Xaa_1$ and $Xaa_2$ are as defined above, may be used as a substrate for the trypsin mutants according to the present invention, e.g. in an effort of peptide ligation or in an effort of C-terminal peptide transacylation, e.g. for modification and/or labeling purposes.

Preferably a target polypeptide according to the present invention consists of 20 to 2000 amino acids. Also preferred is a target peptide consisting of 30 to 1500 amino acids. More preferred such target polypeptide consists of 40-1000 amino acids.

Preferred target polypeptides are polypeptides used in diagnostic or in therapeutic applications.

Preferred target polypeptides for example comprise specific binding agents, like antibodies and fragments thereof. Also preferred are specific binding agents obtainable by phage display (see e.g., Allen, J. B., et al., TIBS 20 (1995) 511-516).

The term antibody refers to a polyclonal antibody, a monoclonal antibody, fragments of such antibodies, as well as to genetic constructs comprising the binding domain of an antibody. Any antibody fragment retaining essentially the same binding properties as the parent antibody can also be used.

Preferably the target polypeptide comprised in a recombinant polypeptide according to the present invention is a therapeutically active polypeptide. Such therapeutically active polypeptide preferably is selected from the group consisting of a therapeutic antibody, erythropoietin and an interferon. Preferably the therapeutic protein is erythropoietin or an interferon.

It is obvious to the skilled artisan that only such polypeptides will be used as target polypeptides which do not comprise the sequence motif $Xaa_1$-$Xaa_2$-His, with $Xaa_1$ and $Xaa_2$ as defined above, as part of their sequence N-terminal to this desired cleavage site. The skilled artisan will have no problems in excluding those polypeptides having a potential cleavage site for a mutated trypsin of the present invention. In the alternative such potential internal cleavage site sequence may be modified by routine mutation and/or cloning techniques to change and/or remove such un-desired internal cleavage site.

In a preferred embodiment the polypeptide according to the present invention which comprises at or close to its C-terminus the sequence $Xaa_1$-$Xaa_2$-His, wherein $Xaa_1$ and $Xaa_2$ are as defined above, is produced by recombinant methods. The skilled artisan will have no problem to engineer any desired target polypeptide which is accessible to recombinant production in a way to comprise at or close to the C-terminus the above defined restriction site of $Xaa_1$-$Xaa_2$-His.

The restriction site peptide according to the present invention at least comprises the amino acids $Xaa_2$ (R or K)-His with $Xaa_2$ at its N-terminus. It may contain additional amino acids C-terminal thereto which facilitate for example recombinant production or easy purification. In a further preferred embodiment the recombinant polypeptide will comprise as part of the restriction site peptide a so-called His-tag at its C-terminal end which allows for an easy purification by well established chromatographic methods, e.g., use of hexa-His and Ni-NTA-chromatography (Hochuli, E., et al., J. Chromatogr. 411 (1987) 177-184).

Preferably the above described trypsin mutants are used in a method for C-terminal acylation of a peptide substrate. As the skilled artisan will appreciate, such peptide substrate will comprise a cleavage site for a mutated trypsin according to this invention and the method will comprise the steps of providing an appropriate peptide substrate, bringing said peptide substrate into contact with a trypsin mutant according to the present invention under conditions allowing for endoproteolytic cleavage after $Xaa_1$ and formation of an endoprotease target peptide-acyl-intermediate, adding an appropriate nucleophile, and upon nucleophilic attack and binding of said nucleophile to the C-terminus of the target peptide releasing the mutated trypsin from the endoprotease target peptide-acyl-intermediate.

Preferably the above-described mutant trypsins and the above-described polypeptides comprising $Xaa_1$-$Xaa_2$-His, with $Xaa_1$ and $Xaa_2$, as defined above, are used in a method of C-terminal polypeptide modification by transacylation, e.g. in a method for peptide ligation. In a preferred embodiment the present invention therefore relates to a method of producing a C-terminally transacylated target peptide comprising the steps of: (a) providing a polypeptide comprising a target peptide and a restriction site peptide comprising the cleavage site $Xaa_1$-$Xaa_2$-His, wherein $Xaa_1$ is L, Y or F, and $Xaa_2$ is R or K, (b) bringing said peptide into contact with a trypsin mutant according to the present invention under conditions allowing for endoproteolytic cleavage after $Xaa_1$ and formation of an endoprotease target peptide-acyl-intermediate, (c) adding an appropriate nucleophile and (d) upon nucleophilic attack and binding of said nucleophile to the C-terminus of the target peptide releasing the mutated trypsin from the endoprotease target peptide-acyl-intermediate.

As used herein, a nucleophile is a molecule that donates a pair of electrons to an electron acceptor, in this case the α-carboxyl carbon of the peptide-acyl-enzyme intermediate, to form a covalent bond.

Preferably the nucleophile is selected from the group consisting of primary amines, imines, secondary amines, thiol and hydroxyl. Suitable nucleophiles for example include amino acids; amino acid derivatives, such as amino acid esters and amino acid amides; amines, such as ammonia, or benzyl amines.

The terms "transacylation" or "transacylated" are used to indicate that the C-terminal amino acid of the target peptide ($Xaa_1$) is bound via covalent bond to the nucleophile. Where the nucleophile is a thiol the transacylation is a thiolation, where the nucleophile comprises a hydroxylic group the transacylation is a esterification and where the nucleophile is an amine the transacylation results in a transamidation. Transamidation reactions are very important and represent a preferred embodiment according to the present invention.

As the skilled artisan will readily appreciate, appropriate nucleophiles may furthermore comprise modifications which introduce desired properties to the C-terminal end of an appropriate target polypeptide. Preferably the present invention relates to a nucleophile comprising a modification that is selected from the group consisting of a peptide, a peptide amide, a label, a labeled amino acid amide, a labeled peptide, a labeled peptide amide, a non-natural amino acid, and polyethylene glycol.

The term label is well-known to the skilled artisan and can be any desired structure of interest. Preferably such label can be selected from any known detectable groups, such as dyes, luminescent labeling groups such as chemiluminescent groups e.g. acridinium esters or dioxetanes, or fluorescent dyes e.g. fluorescein, coumarin, rhodamine, oxazine, resorufin, cyanine and derivatives thereof. Other examples of labeling groups are luminescent metal complexes such as ruthenium or europium complexes, enzymes as used for CEDIA (Cloned Enzyme Donor Immunoassay, e.g. EP-A-0 061 888), and radioisotopes.

Another preferred group of labels of interest for example comprises one partner of a bioaffinity binding pair. While performing an assay this kind of label interacts specifically and preferably non-covalent with the other partner of the bioaffinity binding pair. Examples of suitable binding partners of bioaffinity binding pairs are hapten or antigen/antibody, biotin or biotin analogues such as aminobiotin, iminobiotin or destheiobiotin/avidin or streptavidin, sugar/lectin, nucleic acid or nucleic acid analogue/complementary nucleic acid, receptor/ligand e.g. steroid hormone receptor/steroid hormone. Preferred labels within this group are selected from hapten, antigen and hormone. Especially preferred labels are haptens like digoxin and biotin and analogues thereof.

Another group of preferred modifications are non-natural amino acids and derivatives thereof. Most interesting are non-natural amino acids containing functional groups, which are orthogonal to the natural amino acids, e.g. aldehyde functions, hydrazines, hydrazides, azides, and α-halogen-ketones.

In case the nucleophile comprises polyethylene glycol (PEG), this PEG preferably has a molecular weight in the range of 2,000 Da to 50,000 Da. The PEG may be linear or branched. More preferred the PEG will be in the molecular weight range from 10,000 Da to 40,000 Da. Preferably the nucleophilic group of such nucleophile comprising PEG will be an arginine or a lysine having a free N-terminal α-amino group. This arginine or this lysine also may be the N-terminus of a peptide. Preferably such pegylated nucleophile is selected from the group consisting of Arg-His-PEG, Arg-His-Ala-PEG, Lys-His-PEG, Lys-His-Ala-PEG and Arg-His-Xaa-PEG, wherein Xaa may be any natural or non-natural di-amino carboxylic acid. The PEG-modified di-amino carboxylic acid may comprise one or two PEG molecule(s) bound to one or to both of these amino groups, respectively. The skilled artisan may select or design other appropriate PEG-modified nucleophiles, like a pegylated cysteine and others.

According to procedures known in the state of the art or according to the procedures given in the examples section and armed with the teaching of the present invention, it is now possible to obtain polynucleotide sequences coding for the trypsin mutants of the invention. Preferably the mutated trypsin according to the present invention is expressed as an inactive precursor (zymogen) which is enzymatically cleaved to result in the active enzyme. In a further embodiment the present invention relates to a nucleotide sequence coding for the mutated trypsin comprising an amino acid substitution at position both at K60 and D189, and at least one more amino acid substitution by histidine at position N143 or position E151, respectively.

The present invention further includes an expression vector comprising a nucleic acid sequence according to the present invention operably linked to a promoter sequence capable of directing its expression in a host cell.

Figure 1:
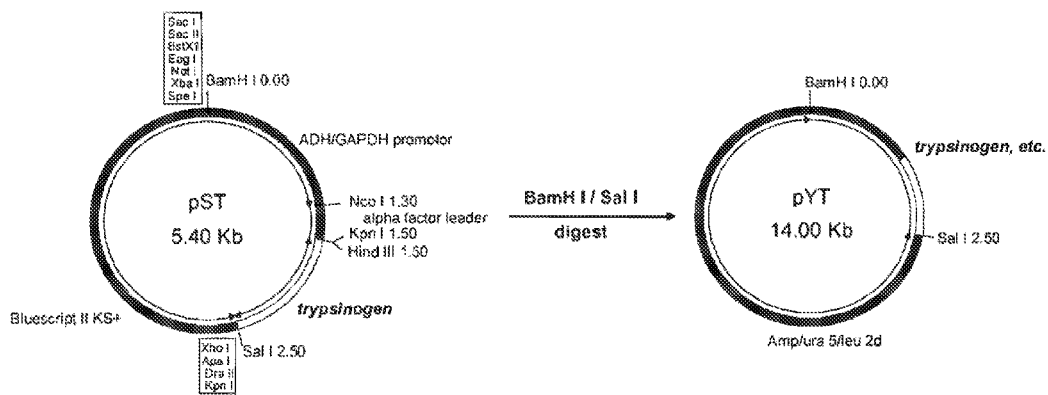
FIG. 1: Cloning vectors used for expression of mutant trypsinogen

The present invention further includes an expression vector comprising a nucleic acid sequence according to the present invention operably linked to a promoter sequence capable of directing its expression in a host cell. Preferred vectors are plasmids such as pST and pYT shown in FIG. 1.

Expression vectors useful in the present invention typically contain an origin of replication, a promoter located upstream in the DNA sequence, and are followed by the DNA sequence coding for a trypsin mutant, followed by transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and the sequences which provide sites for cleavage by restriction endonucleases.

The characteristics of the actual expression vector used must be compatible with the host cell, which is to be employed. For example, when cloning in an E. coli cell system, the expression vector should contain promoters isolated from the genome of E. coli cells (e.g., lac, or trp). Suitable origins of replication in E. coli various hosts include, for example, a ColE1 plasmid replication origin. Suitable promoters include, for example, lac and tip. It is also preferred that the expression vector includes a sequence coding for a selectable marker. The selectable marker is preferably an antibiotic resistance gene. As selectable markers, ampicillin resistance, or canamycin resistance may be conveniently employed. All of these materials are known in the art and are commercially available.

Suitable expression vectors containing the desired coding and control sequences may be constructed using standard recombinant DNA techniques known in the art, many of which are described in Sambrook, J. et al., Molecular Cloning: A Laboratory Manual (1989).

The present invention additionally concerns host cells containing an expression vector which comprises a DNA sequence coding for the mutant trypsin according to the present invention. Preferred are the host cells containing an expression vector comprising one or more regulatory DNA sequences capable of directing the replication and/or the expression of, and operatively linked to a DNA sequence coding for, all or a functional part of mutant trypsin. Suitable host cells include, for example, E. coli HB101 (ATCC 33694) available from Promega (2800 Woods Hollow Road, Madison, Wis., USA), XL1-Blue MRF available from Stratagene (11011 North Torrey Pine Road, La Jolla, Calif., USA) and the like.

Expression vectors may be introduced into host cells by various methods known in the art. For example, transformation of host cells with expression vectors can be carried out by polyethylene glycol mediated protoplast transformation method (Sambrook et al. 1989). However, other methods for introducing expression vectors into host cells, for example, electroporation, bolistic injection, or protoplast fusion, can also be employed.

Once an expression vector containing trypsin mutant has been introduced into an appropriate host cell, the host cell may be cultured under conditions permitting expression of the desired trypsin mutants. Host cells containing an expression vector which contains a DNA sequence coding for the trypsin mutant are, e.g., identified by one or more of the following general approaches: DNA hybridization, the presence or absence of marker gene functions, assessment of the level of transcription as measured by the production of trypsin mRNA transcripts in the host cell, and detection of the gene product immunologically.

It should, of course, be understood that not all expression vectors and DNA regulatory sequences would function equally well to express the DNA sequences of the present invention. Neither will all host cells function equally well with the same expression system. However, one of ordinary skill in the art will make a selection among expression vectors, DNA regulatory sequences, and host cells using the guidance provided herein without undue experimentation.

The following examples are provided to aid the understanding of the present invention, the true scope of which is set forth in the appended claims. It is understood that modifications can be made in the procedures set forth without departing from the spirit of the invention.

Specific Embodiments

EXAMPLE 1

General Procedure of Generating Trypsin Variants

1. Introduction of the desired mutations into trypsin or trypsinogen using a suitable vector comprising the DNA encoding for trypsin or trypsinogen, e.g., a pST vector (cf. FIG. 1).The E. coli vector pST has been originally constructed from L. Hedstrom and represents a yeast shuttle vector containing an ADH/GAPDH-promoter and α-factor leader sequence fused to a sequence encoding for trypsinogen; see: Hedstrom, L., et al., Science 255 (1992) 1249-1253.
2. Transformation of the constructed vector e.g. in *E. coli*.
3. Sub cloning of the modified trypsin-and trypsinogen sequence, respectively, using suitable expression vectors, e.g. yeast vector pYT (cf. FIG. 1). In the case the desired mutation was introduced in this expression vector directly, this step is not needed.
4. Expression of the modified trypsin or trypsinogen in *E. coli* or yeast.
5. Isolation of the modified trypsin or trypsinogen using suitable separation methods, e.g. cation exchange chromatography.
6. In the case trypsinogen has been expressed, the isolated zymogene needs to be activated by limited proteolysis with enterokinase.
7. Final purification of the activated trypsin applying suitable purification methods, e.g. affinity chromatography or anion exchange chromatography.
8. Dialysis In Table 1 the primary sequence of the trypsin variant Tn K60E, E151H, N143H, D189K (corresponding to mutated anionic rat trypsin II, without signal sequence and pro-sequence) is given.

TABLE 1

Basic characteristics of the trypsin variant K60E, N143H, E151H, D183K

| mass | position | peptide sequence (= SEQ ID NO: 1) |
|---|---|---|
| 23828.5978 | 1-223 | IVGGYTCQENSVPYQVSLNS |
|  |  | GYHFCGGSLINDQWVVSAAH |
|  |  | CYESRIQVRLGEHNINVLEG |
|  |  | NEQFVNAAKIIKHPNFDRKT |
|  |  | LNNDIMLIKLSSPVKLNARV |
|  |  | ATVALPSSCAPAGTQCLISG |
|  |  | WGHTLSSGVNHPDLLQCLDA |
|  |  | PLLPQADCEASYPGKITDNM |
|  |  | VCVGFLEGGKKSCQGDSGGP |
|  |  | VVCNGELQGIVSWGYGCALP |
|  |  | DNPGVYTKVCNYVDWIQDTI AAN |

(Mutations are in bold)

Theoretical Peptide Mass:
[Theoretical pI: 5.41/Mw (average mass): 23843.00/Mw (monoisotopic mass): 23827.59]

EXAMPLE 2

Preparation of the Peptides by Means of Solid Phase Peptide Synthesis

Unless specified otherwise the peptides mentioned in this application were synthesized by means of fluorenylmethyloxycarbonyl-(Fmoc)-solid phase peptide synthesis on a batch peptide synthesizer e.g. from Applied Biosystems A433. In each case 4.0 equivalents of the amino acid derivative shown in Table 2 were used for this process.

TABLE 2

| A | Fmoc-Ala-OH |
|---|---|
| C | Fmoc-Cys(Trt)-OH |
| D | Fmoc-Asp(OtBu)-OH |
| E | Fmoc-Glu(OtBu)-OH |
| F | Fmoc-Phe-OH |
| G | Fmoc-Gly-OH |
| H | Fmoc-His(Trt)-OH |
| I | Fmoc-Ile-OH |
| K | Fmoc-Lys(Boc)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pbf)-OH |
| S | Fmoc-Ser(tBu)-OH |
| T | Fmoc-Thr(tBu)-OH |
| V | Fmoc-Val-OH |
| W | Fmoc-Trp-OH |
| Y | Fmoc-Tyr(tBu)-OH |

The amino acid derivatives were dissolved in N-methyl-2-pyrrolidinon. The peptide was synthesized on Wang resin (Wang, S.-S., J. Am. Chem. Soc. 95 (1973) 1328-1333) or on 2-chlortrityl chloride-resin (Barlos, K., et al., Tetrahedron Lett. 30 (1989) 3947-3950). The resin was loaded with 0.5 to 1.0 mMol/g. The coupling reactions were carried out for 20 minutes using 4 equivalents dicyclohexylcarbodiimide and 4 equivalents N-hydroxybenzotriazole in dimethylformamide relative to the Fmoc-amino acid derivative in dimethylformamide as the reaction medium. The Fmoc group was cleaved after each step of the synthesis with 20% piperidine in dimethylformamide for 20 min. Terminal amino groups on the solid phase were optionally acetylated with acetic anhydride.

The introduction of a label e.g. a metal chelate label or a fluorescein label or of a PEG at the C-terminus was carried out during the solid phase synthesis by the direct incorporation of for example a metal chelate or fluorescein coupled amino acid derivative (described in WO 96/03409).

The peptide was released from the support and the acid-labile protective groups were cleaved with 20 ml trifluoroacetic acid, 0.5 ml ethanediol, 1 ml thioanisole, 1.5 g phenol and 1 ml water within 40 min at room temperature. Depending on the amino acid derivatives that were used, it is also possible to use cocktails containing fewer radical traps. 300 ml cooled diisopropyl ether was subsequently added to the reaction solution and was kept for 40 min at 0° C. in order to completely precipitate the peptide. The precipitate was filtered, washed with diisopropyl ether and dissolved in a small amount of 50% acetic acid and lyophilized. The crude material obtained was purified by means of preparative HPLC on Vydac RP C18 218TP152050 (column 50×250 mm, 300 Å; 15 μm) over an appropriate gradient (eluant A: water, 0.1% trifluoroacetic acid, eluant B: acetonitrile, 0.1% trifluoroacetic acid) within ca. 120 min. The eluted material was identified by mass spectrometry.

Alternatively the label, e.g. PEG can also be introduced after cleavage of the peptide from the resin. For this it was advantageous to use a chlortrityl chloride-resin. The protected peptide was cleaved off the resin with 1% trifluoroacetic acid in 10 ml dichloromethane for 20 min at room temperature. Then the C-terminus of the peptide was activated by 2 equivalents dicyclohexylcarbodiimide, 2 equivalents N-hydroxybenzotriazole and 2 equivalents triethylamine in dimethylformamide as reaction medium and one equivalent of the amino acid derivative of the labeling group or the effector group was added. The protective groups are removed by using 20 ml trifluoroacetic acid, 0.5 ml ethanediol, 1 ml thioanisole, 1.5 g phenol and 1 ml water within 40 min at room temperature. Depending on the amino acid derivatives that were used, it is also possible to use cocktails containing fewer radical traps. 300 ml cooled diisopropyl ether was subsequently added to the reaction solution and the reaction solution was kept for 40 min at 0° C. in order to completely precipitate the peptide. The HPLC purification was carried out as described above.

EXAMPLE 3

Transamidation of Ala-Ala-Tyr-Arg-His-Ala-Gly (SEQ ID NO: 2) with Arg-NH$_2$ Catalyzed by the Trypsin Variant Tn K60E, E151H, N143H, D189K The peptide Ala-Ala-Tyr-Arg-His-Ala-Gly (SEQ ID NO: 2) was synthesized by conventional solid-phase peptide synthesis using Fmoc-chemistry and a preloaded Wang-resin as described in Example 2. The respective amino acid building blocks are commercially available and were purchased from various suppliers. Arg-NH$_2$ was a commercial product from Bachem (Switzerland).

1 ml reaction volume containing 1 mM Ala-Ala-Tyr-Arg-His-Ala-Gly (SEQ ID NO: 2) and 5 mM Arg-NH$_2$ dissolved in 0.1 M Hepes buffer pH 8.0; 20 µM trypsin variant Tn K60E, E151H, N143H, D189K; 100 µM ZnCl$_2$ or, alternatively 100 µM EDTA was stirred at 25° C. After defined time intervals aliquots were withdrawn and reaction quenched by addition of 1% trifluoroacetic acid in methanol/water (1:1, v/v) resulting in a final pH of 2 of the withdrawn samples. The latter were analyzed by analytical HPLC giving the time courses of the reactions as shown in FIG. 2. The identity of the final product of synthesis was verified by mass spectroscopy.

EXAMPLE 4

Influence of Zn$^{2+}$ ions on the specificity of the trypsin variant Tn K60E, E151H, N143H, D189K The peptide substrates Bz-Ala-Ala-Tyr-Arg-His-Ala-Ala-Gly (SEQ ID NO: 3), Bz-Ala-Ala-Tyr-Arg-His-Ala-Gly (SEQ ID NO: 4), Bz-Ala-Ala-Tyr-Arg-His-Asp-Ala-Gly (SEQ ID NO: 4), Bz-Ala-Ala-Tyr-Arg-Arg-Ala-Gly (SEQ ID NO: 5), and Bz-Ala-Ala-Tyr-Asp-His-Ala-Gly (SEQ ID NO: 6) was synthesized by conventional solid-phase peptide synthesis using Fmoc-chemistry and a preloaded Wang-resin. The respective amino acid building blocks are commercially available and were purchased from various suppliers.

1 ml reaction volume containing 1 mM of one of the following peptides Bz-Ala-Ala-Tyr-Arg-His-Ala-Ala-Gly (SEQ ID NO: 3), Bz-Ala-Ala-Tyr-Arg-His-Ala-Gly (SEQ ID NO: 4), Bz-Ala-Ala-Tyr-Arg-His-Asp-Ala-Gly (SEQ ID NO: 4), Bz-Ala-Ala-Tyr-Arg-Arg-Ala-Gly (SEQ ID NO: 5) or Bz-Ala-Ala-Tyr-Asp-His-Ala-Gly (SEQ ID NO: 6) dissolved in 0.1 M Pipes/Tris-buffer pH 8.0; 20 µM trypsin variant Tn K60E, E151H, N143H, D189K, 100 µM ZnCl$_2$ or, alternatively EDTA, was stirred at 30.degree. C. After defined time intervals, the reactions were terminated by addition of 1% trifluoroacetic acid in methanol/water (1:1, v/v). The quenched reaction mixtures were analyzed by analytical HPLC. The respective rates of reactions are shown in FIG. 3. The identity of the final products was verified by mass spectroscopy.

EXAMPLE 5

Influence of the Recognition Sequence on the Rate of Reaction Catalyzed by the Trypsin Variant Tn K60E, E151H, N143H, D189K The N$^\alpha$-benzoylated peptides of SEQ ID NOs: 2-18 have been synthesized by conventional solid-phase peptide synthesis using Fmoc-chemistry and a preloaded Wang-resin. The respective amino acid building blocks are commercially available and were purchased from various suppliers.

1 ml reaction volume containing 1 mM N$^\alpha$-benzoylated peptide dissolved in 0.1 M Pipes/Tris-buffer pH 8.0; 20 µM trypsin variant Tn K60E, E151H, N143H, D189K; 100 µM ZnCl$_2$ was stirred at 30° C. After defined time intervals, the reactions were terminated by adding of 1% trifluoroacetic acid in methanol/water (1:1, v/v). The quenched reaction mixtures were analyzed by analytical HPLC. The respective rates of reactions are shown in FIG. 4. The identity of the final products was verified by mass spectroscopy.

As can be easily seen from FIG. 4 the trypsin variant Tn (=K60E, E151H, N143H, and D189K) has a strong preference for a cleavage site comprising L, F or Y in position $P_1$, R or K in position $P_1'$ and His in position $P_2'$.

EXAMPLE 6

Transamidation of Bz-Ala-Ala-Tyr-Arg-His-Ala-Gly (SEQ ID NO: 2) with Arg-His-Ala-Lys(6-CF)—OH (SEQ ID NO: 23) Catalyzed by the Trypsin Variant Tn K60E, E151H, N143H, D189K Bz-Ala-Ala-Tyr-Arg-His-Ala-Gly (SEQ ID NO: 2) has been synthesized by conventional solid-phase peptide synthesis using Fmoc-chemistry and a preloaded Wang-resin. The respective amino acid building blocks are commercially available and were purchased from various suppliers. Arg-His-Ala-Lys(6-CF)—OH (SEQ ID NO: 23) was synthesized by fragment condensation. The protected tripeptide Boc-Arg (Boc)$_2$-His(Trt)-Ala-OH was synthesized on a chlorotrityl-resin using conventional solid phase peptide synthesis. The peptide was cleaved from the resin with 2×40 ml of a cocktail containing methylene chloride/acetic acid/trifluoro acetic acid (v/v/v 8/1/1).

The crude material was purified by reversed phase HPLC. The synthesis of the other fragment, Fmoc-Lys(6-carboxyfluorescein), was performed from 0.6 mmol Fmoc-Lys*HCl, 0,655 mMol 6-carboxyfluorescein (purchased from Molecular Probes) in 3 ml dioxin and 3 ml DMF. The Fmoc-group was cleaved off with piperidine and the crude material purified by reversed phase HPLC. Then the protected tripeptide was activated with 1 equivalent of HBTU (Iris Biotech) and 3 equivalents of diisopropylethylamine in DMF. 1 equivalent of Lys(6-carboxy-fluorescein) was added and the mixture was stirred for 2 h at room temperature. Then the deprotection was done using a deprotection cocktail (18 ml trifluoroacetic acid, 0.5 ml water and 0.5 ml ethandithiol). The peptide was precipitated with diisopropylether, purified by RP-HPLC, and obtained in good yield.

Figure 5:
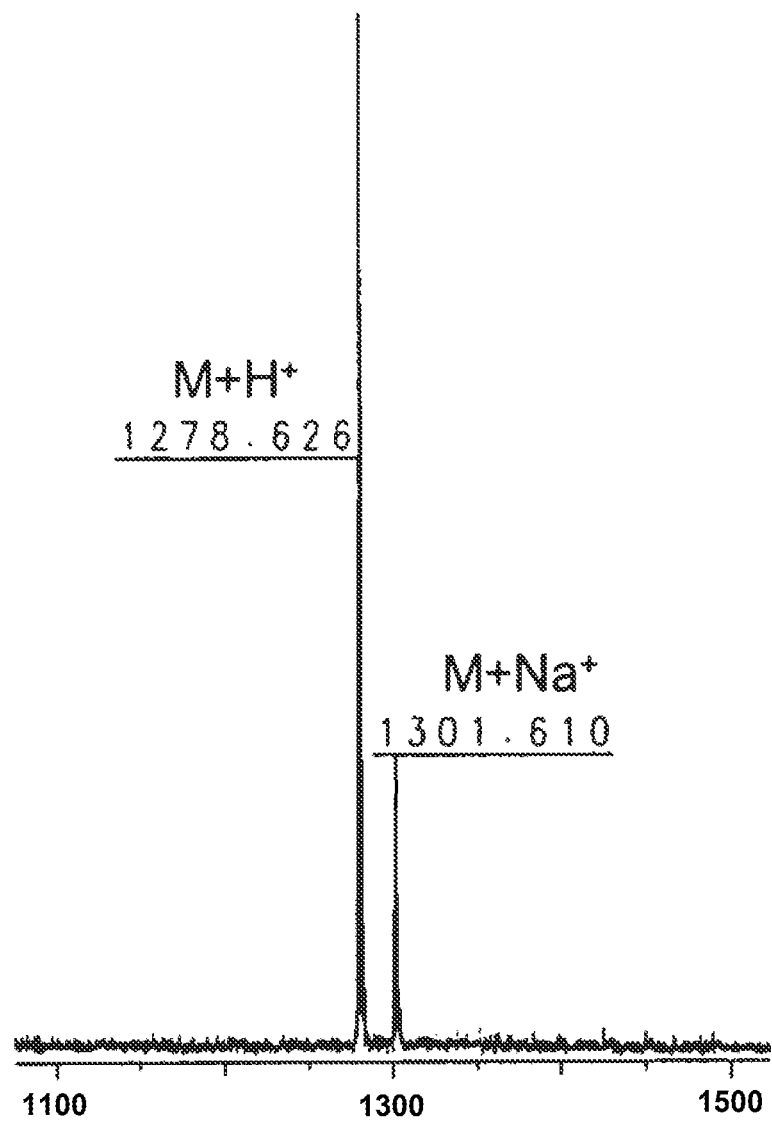

1 ml reaction volume containing 0.5 mM Bz-Ala-Ala-Tyr-Arg-His-Ala-Gly (SEQ ID NO: 20) and 2.5 mM Arg-His-Ala-Lys(6-CF)—OH (SEQ ID NO: 23) dissolved in 0.1 M Pipes/Tris-buffer pH 8.0; 20 µM trypsin variant Tn K60E, E151H, N14311, D189K; 100 µM ZnCl$_2$ or, alternatively 100 µM EDTA, was stirred at 30° C. After defined time intervals respective aliquots were withdrawn and quenched by addition of 1% trifluoroacetic acid in methanol/water (1:1, v/v) resulting in a final pH of 2 of the withdrawn samples. HPLC was used for analyzing the course of reaction and isolating the synthesis product. The latter was obtained in a yield of >99% and has been further analyzed by mass spectroscopy as shown in FIG. 5.

EXAMPLE 7

Transamidation of AKTAAALHIL VKEEKLALDL LEQIICINIGADF GKLAKKHSIC PSGKRGGDLG EFRQGQMVPA FDKVVFSCPV LEPTGPLHTQ FGYHIIKVLY RH (SEQ ID NO: 21) with Arg-His-Gly-PEG catalyzed by the trypsin variant Tn K60E, E151H, N143H, D189K Arg-His-Gly-PEG is synthesized by fragment condensation of Boc-Arg(Boc)$_2$-His(Trt)-Gly-OH and amino-PEG (20 kD) purchased form Nektar/Shearwater. For synthesis of the protected tripeptide and the activation of the fragment see example 6. Here 0.5 equivalents of amino-PEG (20 kD) were used as nucleophile. After deprotection (cocktail see example 6) all low molecular impurities were separated off using RP-HPLC.

The polypeptide AKTAAALHIL VKEEKLALDL LEQIKNGADF GKLAKKHSIC PSGKRGGDLG EFRQGQMVPA FDKVVFSCPV LEPTGPLHTQ FGYHIIKVLY RH (SEQ ID NO: 19), containing the recognition sequence Tyr-Arg-His on its C-terminus, is produced from native *E. coli* parvulin 10 by exchanging the original C-terminal Asn moiety with an artificial His. After expression and purification, the respective modified parvulin 10 (Asn92His) variant is dissolved in Pipes/Tris-buffer pH 8.0. Final concentrations of 20 μM trypsin variant Tn K60E, E151H, N143H, D189K, 100 μM ZnCl$_2$, and an excess of Arg-His-Gly-PEG are added into this reaction mixture. After stifling at 30° C., the reaction is terminated by addition of 1% trifluoroacetic acid in methanol/water (1:1, v/v). Analysis is done by HPLC, gel electrophoresis and/or mass spectroscopy. Isolation of the final product AKTAAALHIL VKEEKLALDL LEQIKNGADF GKLAKKHSIC PSGKRGGDLG EFRQGQMVPA FDKVVFSCPV LEPTGPLHTQ FGYHIIKVLY RH-Gly-PEG (SEQ ID NO: 24) is performed by conventional protein purification techniques, e.g. by chromatographic methods.

What is claimed is:

1. A method of producing a C-terminally transacylated target peptide comprising the steps of:
   providing a polypeptide comprising a target peptide and a restriction site peptide, wherein the restriction site peptide comprises the cleavage site $Xaa_1$-$Xaa_2$-His, wherein $Xaa_1$ is L, Y or F, and $Xaa_2$ is R or K, and wherein said restriction site peptide overlaps with the target peptide by the amino acid $Xaa_1$ at the C-terminal end of said target peptide,
   bringing said polypeptide into contact with a trypsin mutant according to SEQ ID NO:1 or a trypsin mutant having at least 95% identity to SEQ ID NO:1 under conditions allowing for endoproteolytic cleavage after $Xaa_1$, thereby forming an endoprotease target peptide-acyl-intermediate,
   adding an appropriate nucleophile, and,
   upon nucleophilic attack and binding of said nucleophile to the C-terminus of the target peptide, releasing the mutated trypsin from the endoprotease target peptide-acyl-intermediate.

2. The method of claim 1 wherein said nucleophile is selected from the group consisting of a primary amine group, an imine group, a secondary amine group, a thiol group and a hydroxyl group.

3. The method of claim 1 wherein said nucleophile is selected from the group consisting of an amino acid amide, a peptide, a peptide amide, a label, a labeled amino acid amide, a labeled peptide, a labeled peptide amide, and polyethyleneglycol.

4. The method of claim 3 wherein said nucleophile is polyethyleneglycol.

* * * * *